United States Patent [19]

Cantrell

[11] Patent Number: 4,970,593
[45] Date of Patent: Nov. 13, 1990

[54] VIDEO IMAGE ENHANCEMENT UTILIZING A TWO-DIMENSIONAL DIGITAL APERTURE CORRECTION FILTER

[75] Inventor: Clifford B. Cantrell, North Garden, Va.

[73] Assignee: Sperry Marine Inc., Charlottesville, Va.

[21] Appl. No.: 399,733

[22] Filed: Aug. 28, 1989

[51] Int. Cl.⁵ .................... H04N 5/14; H04N 5/204
[52] U.S. Cl. ................................. 358/166; 358/177; 358/37
[58] Field of Search .............. 358/166, 37, 160, 162; 364/726, 624.05, 572; 128/659

[56] References Cited

U.S. PATENT DOCUMENTS

| | | | |
|---|---|---|---|
| 4,330,833 | 5/1983 | Pratte et al. | 358/166 |
| 4,747,157 | 5/1988 | Kurakake et al. | 358/37 |
| 4,764,974 | 8/1988 | Woods | 364/726 |
| 4,805,031 | 2/1989 | Powell | 358/166 |
| 4,811,097 | 3/1989 | Ritter et al. | 364/726 |
| 4,846,187 | 7/1989 | Siegel | 128/659 |
| 4,855,829 | 8/1989 | Kihara | 358/37 |

*Primary Examiner*—Howard W. Britton
*Assistant Examiner*—Michael Lee
*Attorney, Agent, or Firm*—Seymour Levine

[57] ABSTRACT

A video camera system has a modulation transfer function (MTF). Video image data are stored in frame grabbers and converted in a digital signal processor from the image domain to the spatial domain by a two-dimensional digital Fourier transform. The spatial data are filtered by a two-dimensional aperture correction filter that has an MTF inverse to the uncorrected system MTF. The filtered spatical data are converted back into the image domain by a two-dimensional inverse digital Fourier transform. The two-dimensional digital aperture correction filter is stored in the form of software in the digital signal processor.

7 Claims, 4 Drawing Sheets

VIDEO IMAGE ENHANCEMENT UTILIZING A TWO-DIMENSIONAL DIGITAL APERTURE CORRECTION FILTER

BACKGROUND OF THE INVENTION

1. Field of the Invention

The invention relates to video imaging systems with respect to enhancing image detail and clarity.

2. Description of the Prior Art

Optical devices and systems such as lenses, cameras, televsion cameras, video monitors, television systems, filters, and the like, have a response to spatial frequency denoted as the Modulation Transfer Function (MTF). The MTF is a curve of contrast versus spatial frequency. This is analogous to audio devices having a frequency response of amplitude versus frequency.

As is well known, spatial frequency is the reciprocal of the line spacing of a series of equally spaced lines and is traditionally expressed in cycles per millimeter. In order to obtain the MTF of an optical device, a chart with groups of three black bars on a white background is utilized. The difference between the black and white of the bar set, as measured with a photometer, compared with the black to white ratio of an entirely black target compared with an entirely white target is the contrast at the spatial frequency given by the inverse of the bar group spacing.

All optical devices inherently have a non-ideal MTF response curve because of the finite size of the optical aperture associated therewith. The MTF curve of such optical devices is normally a monotonically decreasing function such as a downwardly sloping diagonal line, or the like, that intersects the spatial frequency axis at a point of frequency less than or equal to the diffraction limit. The diffraction limit is the spatial frequency at which the finite size of the optical aperture renders resolution at higher spatial frequencies impossible. Thus, the diffraction limit is the maximum point at which the MTF curve intersects the spatial frequency axis and is therefore the point on the MTF curve at which the contrast or resolution must diminish to zero. Were the aperture of the optical device infinite, the device would not be limited by the diffraction effects associated with the aperture edges.

In an optical system, the MTF curves of all of the devices in the system are multiplied point by point to provide the system MTF curve. Since each of the optical devices comprising the system has a non-ideal response, the system MTF curve is typically a downwardly sloping function diminishing to zero contrast or resolution at the diffraction limit. The downwardly sloping characteristic of the typical MTF response results in a gradual loss of contrast in the detail of the image as the detail becomes finer and finer until the diffraction limit is attained. An Aperture Correction Filter (ACF) is a device that endeavors to compensate for the diffraction effects of the finite size of the optical aperture of the system. The ACF ideally has an MTF curve that is the inverse of the system MTF curve such that when the ACF is included in the system, the composite MTF curve is substantially flat out to the diffraction limit. The ACF provides a boost in the high spatial frequency contrast to compensate for the decreasing characteristic of the system MTF curve. An ACF is to an optical system what an audio equalizer is to an audio system; viz, compensating for the inadequate frequency response of the system.

The ideal MTF curve for an ACF is the point-by-point reciprocal of the contrast of the MTF curve of the optical system without the ACF. Ideally, the MTF of the system with the ACF is 100% from a spatial frequency of zero out to the diffraction limit of the worst component of the system, which usually is the first element. Further contrast boost beyond the system diffraction limit is ineffective since improvement beyond this spatial frequency is impossible. The system with the ACF as compared to the system without the ACF provides more pronounced detail and therefore produces a visually better, sharper image.

In the prior art, the ACF function has been implemented in television camera systems as an electronic high pass filter on the raster scanned video. This technique boosted the high spatial frequency response of the system tending to compensate for the finite aperture of the camera system. The technique operates and has an effect only on the horizontal axis and is therefore only one dimensional. Such a one dimensional filter does not effect any improvement with respect to fine detail resolution in the vertical dimension. It is extremely difficult to implement a vertical ACF. Prior art aperture correction filters utilizing electronic circuitry tended to be undesirably complex, bulky and expensive. Such prior art filters were difficult to design and it was furthermore difficult to alter the filter characteristics thereof.

The following U.S. patents exemplify the state of the art: 4,080,627; 4,097,897; 4,110,790; 4,160,265; 4,160,276; 4,200,888; 4,328,772; 4,275,417; 4,336,552; 4,402,006; 4,410,912; 4,481,537; 4,524,379; 4,623,923; 4,691,366; 4,709,393; and 4,714,958. Many of the devices of these patents suffer from the defect of providing an affect only in the horizontal dimension. Other devices combine a vertical ACF with a horizontal ACF utilizing undesirably complex, expensive, bulky and slow techniques and apparatus.

SUMMARY OF THE INVENTION

The present invention overcomes the disadvantages of the prior art by providing apparatus for enhancing the image of a video system, the system having a two-dimensional system Modulation Transfer Function (MTF). A video source provides two-dimensional video image signals to digital storage means. The digital storage means stores two-dimensional frame signals from a frame of the video image signals, the frame signals being in digital format. A two-dimensional digital Aperture Correction Filter (ACF) has a two-dimensional filter MTF that is the inverse of the system MTF. The ACF provides digital two-dimensional ACF signals in accordance with the filter MTF. Digital signal processing means combines the two-dimensional frame signals with the two-dimensional ACF signals to provide enhanced two-dimensional video image signals so that the system with the ACF has a substantially flat MTF. Preferably, the frame signals in the image domain are converted to signals in the spatial frequency domain by a two-dimensional digital Fourier transform. The ACF signals, in spatial domain format, are multiplied point by point with the spatial frequency frame signals. The so-processed signals in the spatial domain are converted to the image domain by a two-dimensional inverse digital Fourier transform.

BRIEF DESCRIPTION OF THE DRAWINGS

FIG. 4 is a schematic representation of the video image domain useful in explaining the operation of the present invention.

DESCRIPTION OF THE PREFERRED EMBODIMENTS

Figure 1:
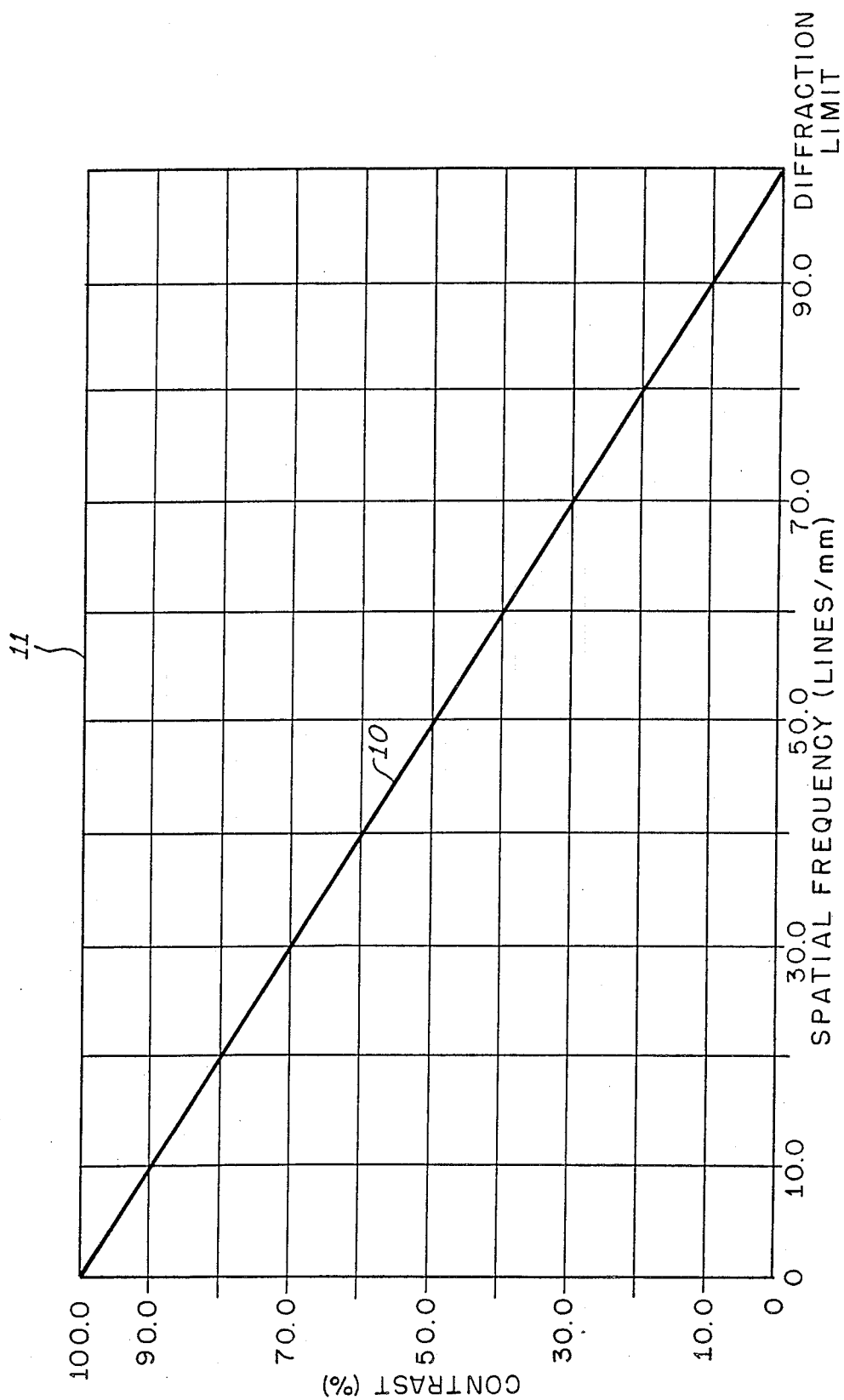
FIG. 1 is a graph illustrating a typical one-dimensional MTF curve of an optical system and the ideal MTF curve therefor.
Figure 2:
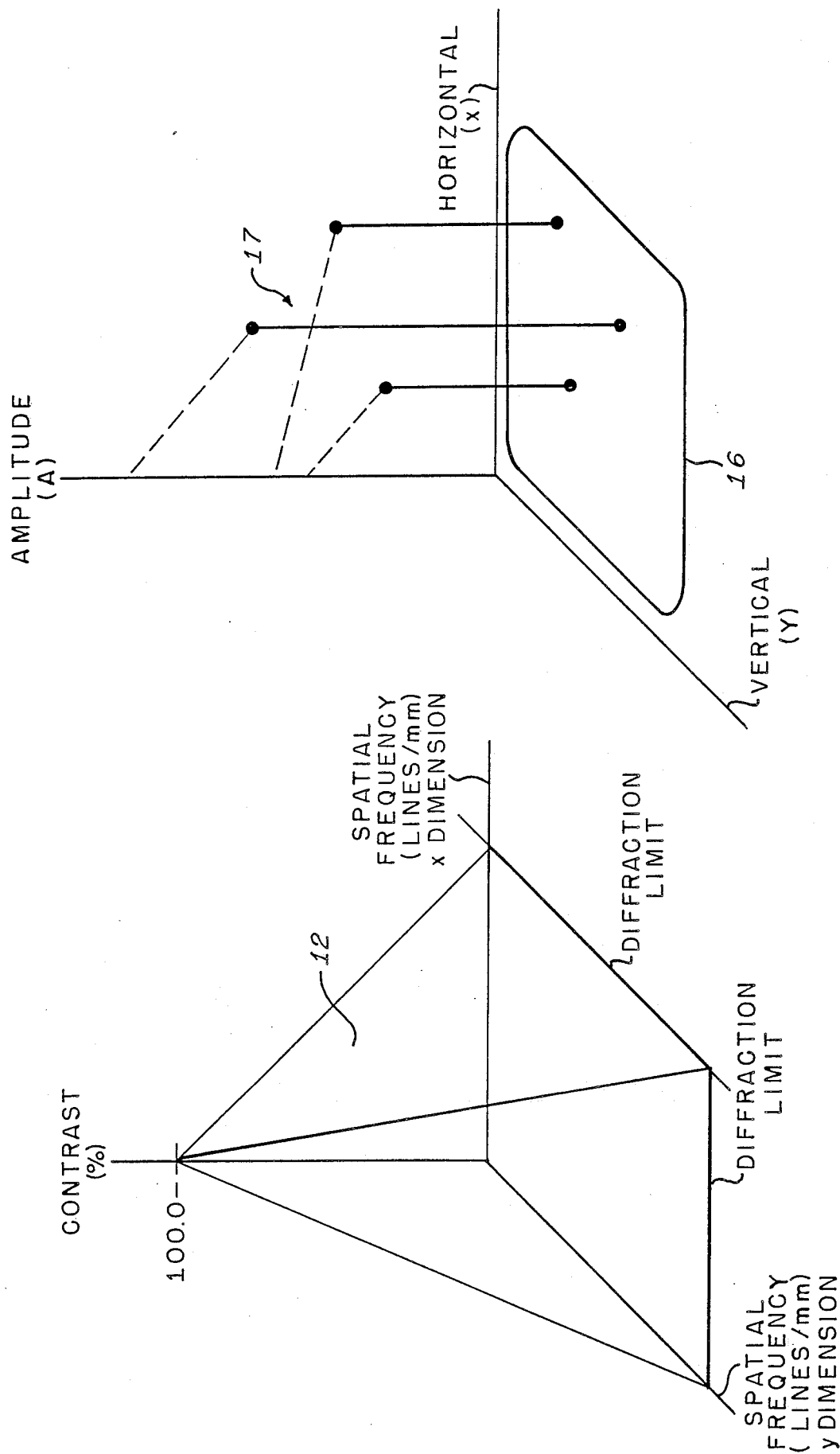
FIG. 2 is a diagram illustrating a typical two-dimensional MTF surface corresponding to the typical MTF curve of FIG. 1.

The invention described herein utilizes a digital computer to enhance the image produced by a video camera system such as the type utilized in surveillance applications. Referring to FIG. 1, a typical MTF curve 10 is illustrated. The curve 10 may be that of a typical lens. For comparison, an ideal MTF curve 11 is illustrated therefor. It is appreciated that the MTF curve 10 rolls off from a contrast of 100% at zero spatial frequency to zero percent contrast at the diffraction limit. FIG. 2 illustrates a two-dimensional MTF surface 12 corresponding to the MTF curve 10 of FIG. 1. It is appreciated that FIG. 2 represents the MTF surface 12 in the spatial frequency (SF) domain.

Figure 3:
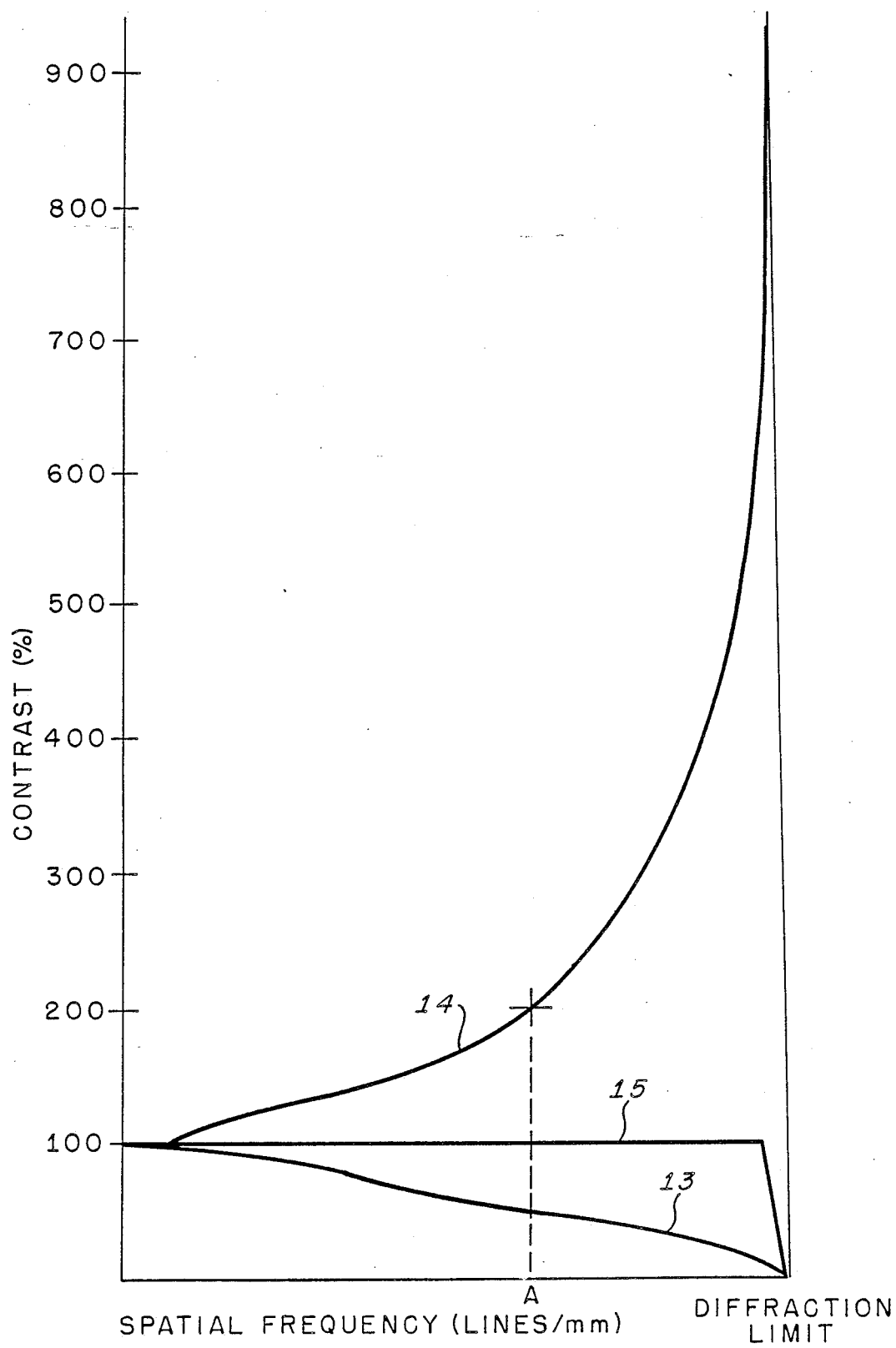
FIG. 3 is a graph illustrating the MTF curve of an uncorrected system along with the MTF curve of an aperture correction filter that would yield an ideal MTF curve for the corrected system.

Referring to FIG. 3, system MTF curves are illustrated. A curve 13 depicts the MTF of an uncorrected system. A curve 14 depicts the MTF of an Aperture Correction Filter for the uncorrected system of curve 13. A curve 15 illustrates the corrected system MTF resulting from applying the Aperture Correction Filter MTF of curve 14 to the uncorrected system MTF of curve 13. It is appreciated that the curve 14 is derived by taking the point-by-point reciprocal of the curve 13. For example, at the spatial frequency of a point A, the contrast of the uncorrected system is 50%. The corresponding reciprocal point on the curve 14 is 200%.

Referring to FIG. 4, a diagram of the video image domain is illustrated. The horizontal (X) and vertical (Y) dimensions are shown with a typical frame 16 illustrated therein. Each pixel of the frame 16 has a video intensity or amplitude associated therewith represented in the amplitude dimension (A). These amplitude points form a two-dimensional surface 17 in the image domain of FIG. 4 in accordance with the video information in the frame 16. It is appreciated that a two-dimensional Fourier transform will map the surface 17 in the image space of FIG. 4 into an equivalent surface in the spatial frequency domain of FIG. 2. Conversely, a two-dimensional inverse Fourier transform maps the surface in the spatial frequency domain of FIG. 2 into an equivalent surface 17 in the image space of FIG. 4.

Figure 5:
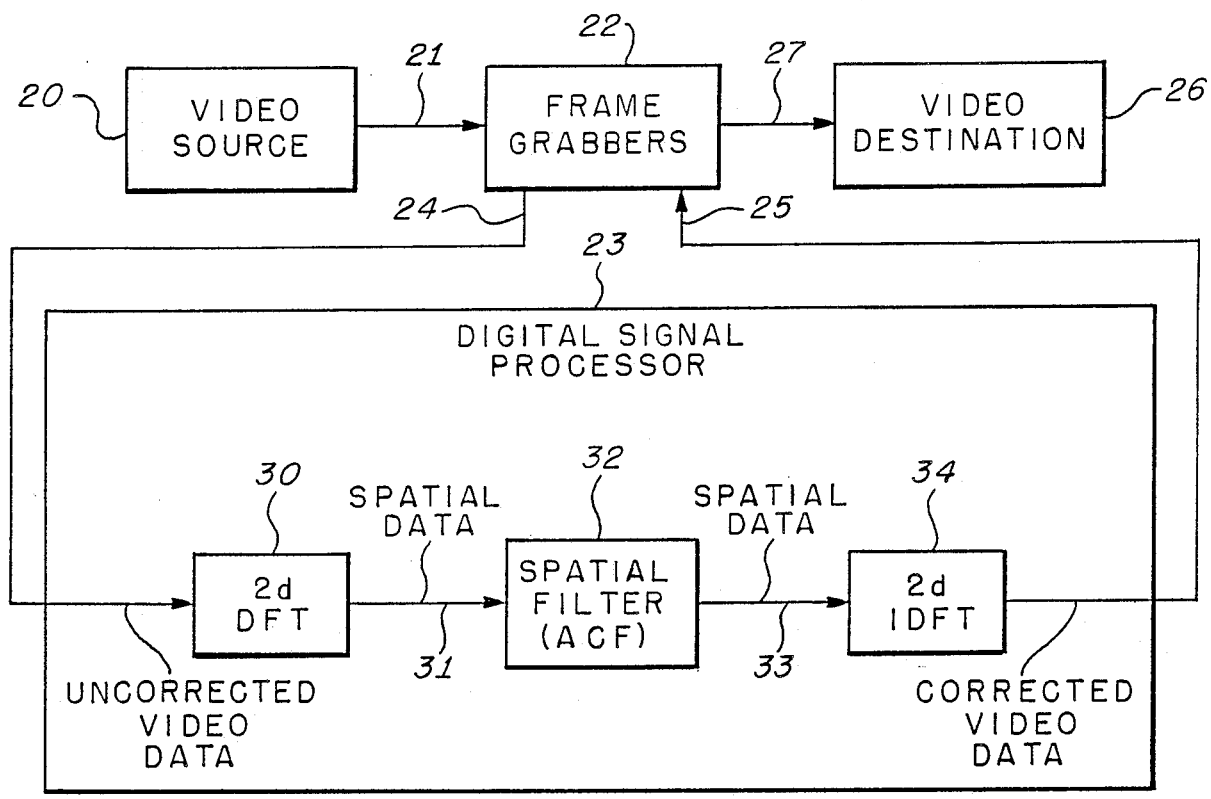
FIG. 5 is a schematic block diagram of the preferred implementation of the present invention.

Referring to FIG. 5, a schematic block diagram of a preferred embodiment of the invention is illustrated. A video source 20 provides video image data on a path 21. The video source 20 comprises any source of video data such as a video camera that provides real time video image signals or a video tape player that provides previously recorded image data. The video source 20 provides a video image that is transferred to frame grabbers 22 via the path 21. The frame grabbers 22 are commercially procurable devices for storing one or more frames of video image data in digital format. The video source 20 provides the video data in a conventional format that should be compatible with the frame grabbers utilized. The frame grabbers 22 capture and store the video image data from the video source 20 for processing in a digital signal processor 23. The digital image data from the frame grabbers 22 are transferred for processing to the digital signal processor 23 via a path 24. The digital signal processor 23 operates on the data stored in the frame grabbers 22 in a manner to be described, and transfers the processed frame data back to the frame grabbers 22 via a path 25. Thus, the frame grabbers 22 hold the digital video image data while the digital signal processor 23 executes processing thereon. The processed video image is provided by the frame grabbers 22 to a video destination 26 via a path 27. The video destination 26 is any conventional device for displaying, recording, or further manipulating the video data. Preferably, the video destination 26 comprises either a conventional video monitor or a video recording device such as a video tape recorder.

The frame grabbers 22 comprise one or a plurality of frame grabbers. Only one frame grabber is required for operation of the system. A frame is entered into the frame grabber from the video source 20 and the data therein is processed by the digital signal processor 23 and transferred back into the frame grabber via the path 25. The frame grabber 22 then holds the output image which is provided to the video destination 26 for, for example, display. Although only one frame grabber may be utilized for operation, a plurality of frame grabbers are employed for real time processing. One frame grabber cannot simultaneously capture a frame image, process it, and transfer it to the video destination output device 26 in real time. Thus, a plurality of frame grabbers are utilized to provide real time processing of sequentially occurring video frames. Two or three frame grabbers are utilized so that the digital signal processor 23 operates without interferring with the input or output images. In a three frame grabber system, a first frame grabber accepts the input image, a second frame grabber provides the image data on which the processor 23 operates and a third frame grabber holds the output image for transfer to the video destination 26. The three frame grabber system can be reduced to two frame grabbers utilizing a commercially available two frame grabber configuration. The first frame grabber holds part of the input image and part of the output image. The second frame grabber is utilized for processing the video data.

The digital signal processor 23 includes a function 30 for performing a two-dimensional digital Fourier transform (DFT). Preferably, a two-dimensional fast Fourier transform (FFT) is performed by the function 30. The function 30 effects a two-dimensional digital Fourier transformation of the uncorrected video image data from the video source 20 on the path 24 into spatial data on a path 31. The tranformed spatial data on the path 31 is in the format of amplitude versus spatial frequency. Thus, the video image data in the frame grabber 22 is processed through the two-dimensional digital Fourier transform function 30 to provide the spatial data on the path 31. The function 30 converts the data on the path 24 from the image domain of FIG. 4 into the spatial frequency (SF) domain of FIG. 2.

The image transformed by the function 30 into spatial data is multiplied by a spatial Aperture Correction Filter function 32. The function 32 provides the modulation transfer function of the ACF required to provide the ideal system MTF. Since the transformed image on the path 31 is in the SF domain, the function 32 performs a pixel-by-pixel multiplication of the transformed image with the SF format of the ACF 32 to provide a filtered version of the image in the SF domain on a path 33. Thus, the transformed image on the path 31 is multiplied by the ACF 32 which is a two-dimensional array representing the required horizontal and vertical corrections.

The spatial data on the path 33 is applied to a two-dimensional inverse digital Fourier transform function (IDFT) 34 to transform the spatial data on the path 33 back into image data on the path 25. Thus, the function 34 tranforms the filtered image on the path 33 from the SF domain back to the image domain on the path 25. The signals on the path 25 therefore comprise corrected output video data suitable for transfer to the video destination 26.

Figure 6:
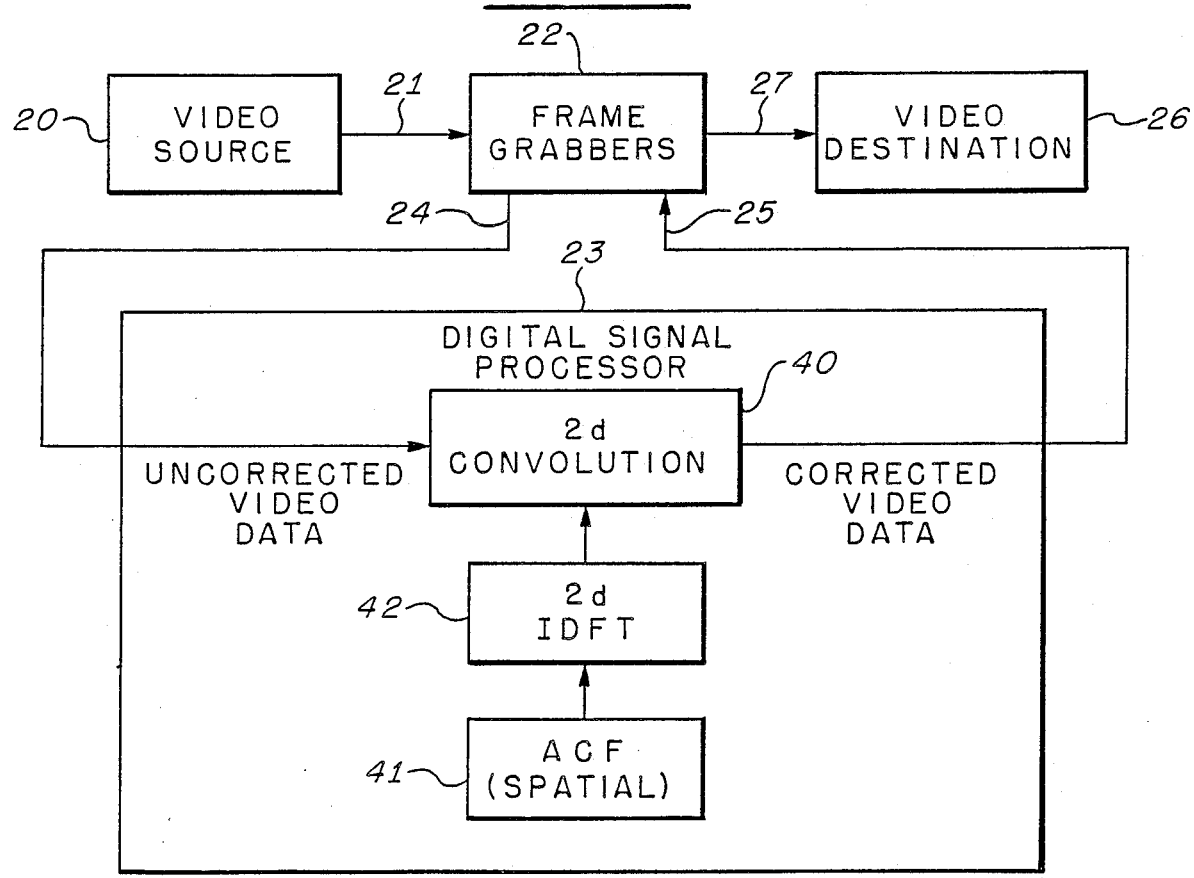
FIG. 6 is a schematic block diagram of an alternative implementation of the present invention.

Referring to FIG. 6, in which like reference numerals designate like components with respect to FIG. 5, an alternative embodiment of the invention is illustrated. In the embodiment of FIG. 6, the uncorrected video image data on the path 24 is filtered by a two-dimensional convolution function 40 to provide the corrected video data on the path 25. The function 40 performs a two-dimensional convolution of the original image with an appropriate ACF 41 transformed into the image domain by a two-dimensional inverse digital Fourier transform function 42. Thus, the convolution function 40 directly filters the data on the path 24 in the image domain to provide the filtered image on the path 25 also in the image domain. It is appreciated that once the ACF 41 is obtained and transformed into the image domain by the IDFT 42, the image domain version of the ACF is stored in the digital signal processor 23 for use by the convolution function 40 in filtering video image data on the path 24. Thus, the two-dimensional array of the image, which is represented by a surface, such as the surface 17 of FIG. 4, is convolved by the function 40 with the ACF surface in the image domain.

It is appreciated with respect to FIG. 5, that the spatial filter 32 includes the two-dimensional array of ACF corrections as well as means for performing a pixel-by-pixel multiplication of these corrections with the two-dimensional spatial data on the path 31. The ACF 41 of FIG. 6 includes the two-dimensional array of spatial ACF data which is converted to image data by the IDFT 42. The convolution function 40 then utilizes the two-dimensional image surface provided by the IDFT 42 to perform the convolution against the two-dimensional image surface on the path 24.

The ACF 32 and 41 are created by measuring the MTF of the uncorrected optical system utilizing a conventional method and inverting (1/pixel) this MTF curve on a pixel-by-pixel basis to provide the spatial frequency domain version of the desired ACF. Utilizing this ACF, provides a flat corrected system MTF out to the diffraction limit.

A conventional method of measuring MTF is to utilize a graduated series of bar charts, either square wave or sinusoidal, and to measure the difference in the video between the black areas and the white background with, for example, an oscilloscope. This process is repeated for both the horizontal and vertical dimensions assuming that the MTF is constant across each dimension. The two one-dimensional curves are combined in the respective dimensions thereof to create a two-dimensional surface. This two-dimensional surface is the spatial frequency domain representation of the response of the optical system.

This process is automated by utilizing the image processor 23 to calculate the values for the ACF from a specially derived standard chart. The chart contains a full graduated series of bars in both dimensions in predetermined locations. The image processor 23 examines these locations to obtain data to generate the MTF curves. The processor 23 then utilizes the process described to generate the SF domain representation of the ACF.

Although the FFT and the inverse thereof is the preferred mode of practicing the invention, other transform techiques may be utilized in mapping between the image domain and the SF domain. Although these techniques are not as fast as the FFT, they could be utilized in practicing the invention. Such techniques include the standard digital Fourier transform and the Hartley transform.

The image that results from the processing described herein has image data amplified at the higher spatial frequencies such that a viewer perceives improved clarity of detail in the image. The processing can be applied to either live video or to previously recorded video data. By utilizing the standard chart and method described herein, the ACF is readily tailored to new optical components or different video sources. As described above, the ACF tailoring process can be automated. This contrasts to previous technologies where it was difficult to design the filter and equally difficult to alter the filter characteristics. The present invention, for the first time, renders a software ACF a practical reality that can be utilized to construct a better ACF filter than in the prior art and additionally, permits the ACF to be two-dimensional. The invention provides ACF filters that would be impossible to realize in either optical or electrical implementations. Thus, the present invention provides a new and improved system for enhancing the images from video sources. The video source, such as a video camera, the frame grabber, the digital signal processor, and the video destination, such as a video monitor or video tape recorder are utilized to implement the enhanced system. The digital signal processor operates on the data stored in the frame grabber and updates the data to provide corrected data. The corrected image is displayed on a monitor with enhanced detail. The detail is enhanced such that the system MTF is nearly ideal.

While the invention has been described in its preferred embodiment, it is to be understood that the words which have been used are words of description rather than limitation and that changes may be made within the purview of the appended claims without departing from the true scope and spirit of the invention in its broader aspects.

I claim:

1. Apparatus for enhancing the image of a video system, said system having a two-dimensional system Modulation Transfer Function (MTF), said MTF spanning from substantially zero spatial frequency to the diffraction limit thereof, comprising a source of two-dimensional video image signals, digital storage means for storing two-dimensional frame signals from at least one frame of said video image signals, said frame signals being in digital format, two-dimensional digital Aperture Correction Filter (ACF) means having a two-dimensional filter MTF that consists solely of the inverse of said system MTF from substantially zero spatial frequency to said diffraction limit, said ACF means providing digital two-dimensional ACF signals in accordance with said filter MTF, and digital signal processing means for combining said two-dimensional frame signals with said two-dimensional ACF signals to provide enhanced two-dimensional video image signals so that said system with said ACF has a substantially flat MTF substantially out to said diffraction limit.

2. The apparatus of claim 1 wherein said digital storage means comprises frame grabber means.

3. The apparatus of claim 1 wherein said digital signal processing means comprises first transform means responsive to said two-dimensional frame signals for transforming said two-dimensional frame signals from the image domain to the spatial frequency domain thereby providing spatial image data, spatial filter means responsive to said ACF signals and said spatial image data for multiplying said spatial image data with said ACF signals to provide spatial filtered image data, and second transform means providing a transform inverse to said first transform means responsive to said spatial filtered image data for transforming said spatial filtered image data from the spatial frequency domain to the image domain.

4. The apparatus of claim 3 wherein said first transform means comprises a two-dimensional digital Fourier transform function, and said second transform means comprises a two-dimensional inverse digital Fourier transform function.

5. The apparatus of claim 4 wherein said two-dimensional digital Fourier transform function comprises a fast Fourier transform, and said two-dimensional inverse digital Fourier transform function comprises an inverse fast Fourier transform.

6. The apparatus of claim 1 wherein said digital signal processing means includes convolution means responsive to said frame signals for performing a two-dimensional convolution of said frame signals with said ACF signals in the image domain.

7. The apparatus of claim 1 wherein said two-dimensional digital aperture correction filter means comprises software stored in said digital signal processing means.

* * * * *